(12) United States Patent
Zangooie et al.

(10) Patent No.: US 8,080,849 B2
(45) Date of Patent: Dec. 20, 2011

(54) CHARACTERIZING FILMS USING OPTICAL FILTER PSEUDO SUBSTRATE

(75) Inventors: Shahin Zangooie, Hopewell Junction, NY (US); Lin Zhou, LaGrangeville, NY (US); Sean D. Burns, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 849 days.

(21) Appl. No.: 12/015,795

(22) Filed: Jan. 17, 2008

(65) Prior Publication Data

US 2009/0186427 A1 Jul. 23, 2009

(51) Int. Cl.
*H01L 21/00* (2006.01)
(52) U.S. Cl. .................. 257/347; 257/65; 356/620
(58) Field of Classification Search .......... 257/347, 257/65; 356/620
See application file for complete search history.

(56) References Cited

U.S. PATENT DOCUMENTS

| | | | |
|---|---|---|---|
| 5,696,629 A | 12/1997 | Berger et al. | |
| 6,160,834 A * | 12/2000 | Scott | 372/96 |
| 6,319,333 B1 | 11/2001 | Noble | |
| 6,322,938 B1 | 11/2001 | Cohn | |
| 6,376,267 B1 * | 4/2002 | Noack et al. | 438/16 |
| 6,679,946 B1 * | 1/2004 | Jackson et al. | 117/84 |
| 6,727,995 B1 * | 4/2004 | Halliyal et al. | 356/630 |
| 6,847,463 B2 * | 1/2005 | Malinowski | 356/630 |
| 6,972,438 B2 | 12/2005 | Li et al. | |
| 7,052,921 B1 * | 5/2006 | Plat et al. | 438/14 |
| 7,187,837 B2 * | 3/2007 | Gothoskar et al. | 385/131 |
| 7,427,457 B1 * | 9/2008 | Plat et al. | 430/5 |
| 7,482,177 B2 * | 1/2009 | Imai | 438/7 |
| 7,579,590 B2 * | 8/2009 | Jiang et al. | 250/309 |
| 7,808,657 B2 * | 10/2010 | Zangooie et al. | 356/620 |
| 2003/0068665 A1 | 4/2003 | Kawamura et al. | |
| 2004/0063214 A1 | 4/2004 | Berlin et al. | 436/94 |
| 2004/0142484 A1 * | 7/2004 | Berlin et al. | 436/171 |
| 2005/0189591 A1 * | 9/2005 | Gothoskar et al. | 257/347 |
| 2007/0196011 A1 * | 8/2007 | Cox et al. | 382/145 |
| 2009/0002721 A1 * | 1/2009 | Zangooie et al. | 356/620 |
| 2009/0147364 A1 * | 6/2009 | Kotoku et al. | 359/584 |
| 2009/0186427 A1 * | 7/2009 | Zangooie et al. | 438/16 |
| 2010/0149505 A1 * | 6/2010 | Sewell et al. | 355/67 |
| 2010/0187126 A1 * | 7/2010 | Sendelbach et al. | 205/686 |

* cited by examiner

*Primary Examiner* — Laura Menz
(74) *Attorney, Agent, or Firm* — Ian Mackinnon; Hoffman Warnick LLC

(57) ABSTRACT

A system and method of characterizing a parameter of an ultra thin film, such as a gate oxide layer. A system is disclosed that includes a structure having a pseudo substrate positioned below an ultra thin film, wherein the pseudo substrate includes an optical mirror for enhancing an optical response; and a system for characterizing the ultra thin film by applying a light source to the ultra thin film and analyzing the optical response.

8 Claims, 5 Drawing Sheets

CHARACTERIZING FILMS USING OPTICAL FILTER PSEUDO SUBSTRATE

FIELD OF THE INVENTION

This disclosure relates generally to characterizing parameters of very thin layers, and more particularly relates to a system and method of measuring and controlling a thickness of a gate oxide layer in a semiconductor device using an optical filter pseudo substrate, such as a Bragg reflector.

BACKGROUND OF THE INVENTION

In the semiconductor industry, there is a continuing trend toward manufacturing integrated circuits with a greater number of layers and with higher device densities. To achieve these high densities there have been, and continue to be, efforts towards reducing the thickness of layers, improving the uniformity of layers, reducing the thickness of devices and scaling down device dimensions (e.g., at sub micron levels) on semiconductor wafers. In order to accomplish higher device packing densities, thinner layers, more uniform layers, smaller feature sizes, and smaller separations between features are required. This can include the thickness of gate oxide materials, (e.g., silicon oxide, metal oxides and high K materials such as $ZrO_2$ and $HfO_2$, etc.), interconnecting lines, spacing and diameter of contact holes, and the surface geometry such as corners and edges of various features.

The process of manufacturing semiconductors, or integrated circuits (commonly called ICs, or chips), typically consists of more than a hundred steps, during which hundreds of copies of an integrated circuit can be formed on a single wafer. Generally, the process involves creating several layers on and in a substrate that ultimately forms the complete integrated circuit. This layering process can create electrically active regions in and on the semiconductor wafer surface. Insulation and conductivity between such electrically active regions can be important to reliable operation of such integrated circuits. Thus, controlling the width, thickness and/or uniformity of layers created during the layering process can be important to the reliable operation of such integrated circuits.

Insulation and conductivity between electrically active regions is particularly important in MOSFET (Metal Oxide Semiconductor Field Effect Transistor) semiconductor devices. MOSFET devices typically include a gate separated from a substrate by a gate oxide. The thickness of the gate oxide can be important to reliable operation of the MOSFET, and thus, manufacturing the gate oxide to precise measurements facilitates increased MOSFET reliability. The gate oxide layer functions as an insulating layer, and can be the smallest feature of a device. Reducing the thickness of the gate oxide layer can contribute to increasing the switching speed of a transistor. However, reducing the thickness of the gate oxide layer can lead to problems associated with breakdown and reliability of gate oxides. Thus, precisely monitoring and controlling properties of the gate oxide layer including, but not limited to, thickness and uniformity, are important to facilitating reliable operation of the MOSFET. For example, the ability to store data, to retain data, to be erased, to be reprogrammed and to operate in desired electrical and temperature ranges can be affected by the thickness and/or uniformity of the gate oxide layer. However, due to non-uniform and uncontrolled gate oxide layer formation and inaccurate gate oxide layer formation monitoring techniques, a thickness of gate oxide may be formed greater or lesser than the thickness desired.

U.S. Pat. No. 6,727,995 issued to Halliyal et al. on Apr. 27, 2004, entitled "Gate Oxide Thickness Measurement and Control using Scatterometry," which is hereby incorporated by reference, discloses a technique for regulating gate oxide thickness using reflected light to measure thickness and uniformity. However, such systems have detection limitations that limit the ability to measure ultra thin layers. Accordingly, a need exists for a solution that can characterize parameters, such as thicknesses, of ultra thin layers (i.e., films).

SUMMARY OF THE INVENTION

The present disclosure provides a system for characterizing a film, the system including: a structure having: a substrate; and a pseudo substrate positioned below the film and over the substrate, wherein the pseudo substrate includes an optical mirror for enhancing an optical response, wherein the optical mirror includes a Bragg reflector having at least one period, the at least one period including: a layer formed substantially of silicon; and a layer formed substantially of thermal silicon dioxide underlying the layer formed substantially of silicon, wherein a thickness of the layer formed substantially of silicon and a thickness of the layer formed substantially of thermal silicon dioxide have a thickness relationship according to: $d_L * n_L = d_H * n_H = \lambda/4$; where $d_H$ is a thickness of the layer formed substantially of silicon, $d_L$ is a thickness of the layer formed substantially of thermal silicon dioxide, where $n_H$ is an index of refraction of the layer formed substantially of silicon, $n_L$, is an index of refraction of the layer formed substantially of thermal silicon dioxide, and $\lambda$ is a wavelength corresponding to a reflectance maxima; and a system for characterizing a parameter of the film by applying a light source to the film and analyzing the optical response.

In a second embodiment, there is a method of measuring an ultra thin film, comprising: forming a pseudo substrate, wherein the pseudo substrate includes an optical mirror for enhancing an optical response; forming the ultra thin film on the pseudo substrate; and measuring a thickness of the ultra thin film by applying a light source to the ultra thin film and analyzing the optical response.

In a third embodiment, there is a method of forming a gate oxide layer in a semiconductor device, comprising: forming an optical mirror on a silicon wafer; forming a gate oxide layer on the optical mirror; and characterizing a parameter of the gate oxide layer by applying a light source to the gate oxide layer and analyzing an optical response that is enhanced by the optical mirror.

The illustrative aspects of the present invention are designed to solve the problems herein described and other problems not specifically discussed herein.

BRIEF DESCRIPTION OF THE DRAWINGS

These and other features of this invention will be more readily understood from the following detailed description of the various aspects of the invention taken in conjunction with the accompanying drawings.

Figure 1:
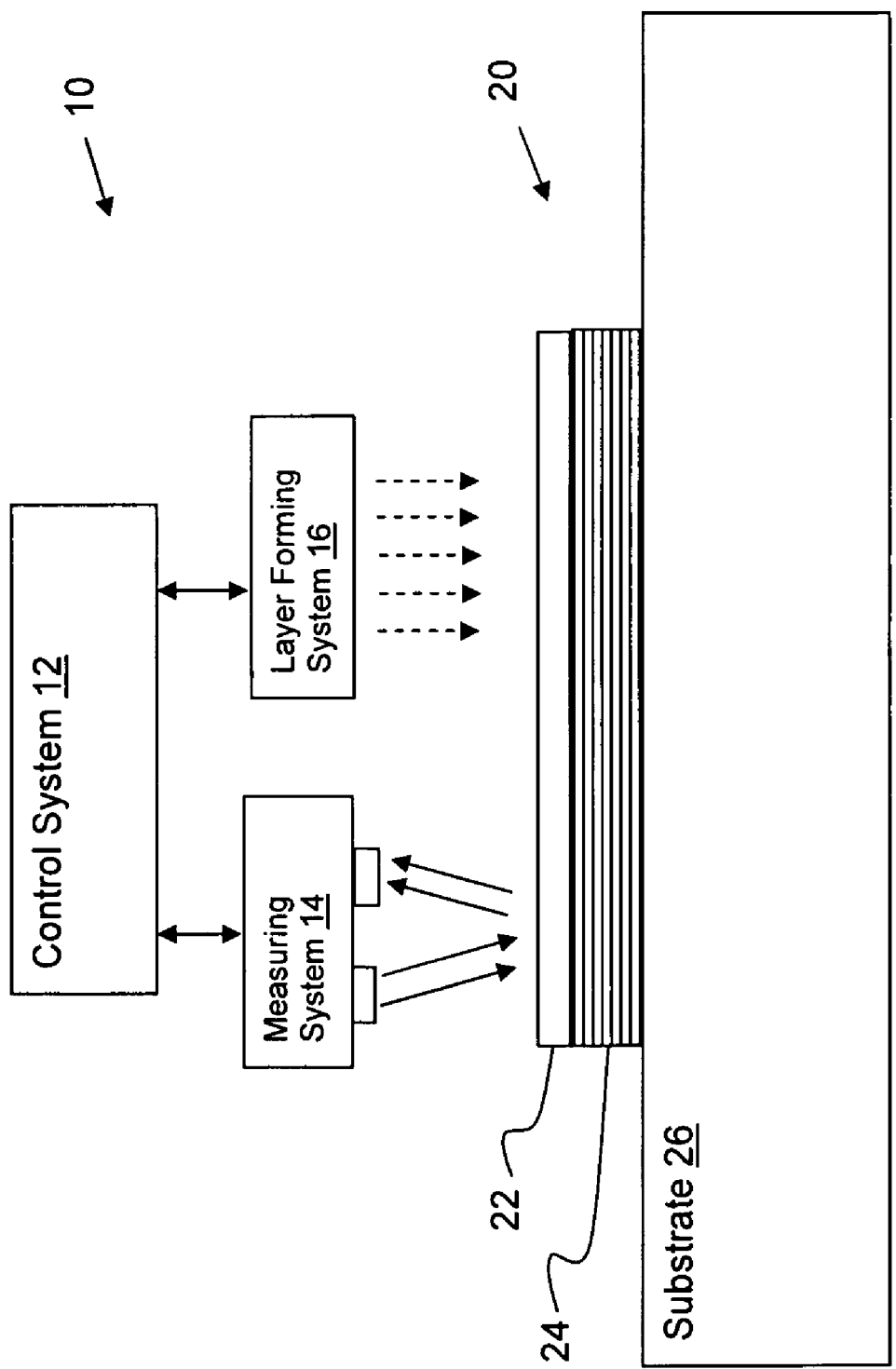
FIG. 1 depicts a wafer being processed with a layer forming system in accordance with an embodiment of the present invention.

The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

Referring now to the drawings, FIG. 1 depicts a device 20 being processed with a processing system 10. In this illustrative embodiment, device 20 represents an integrated circuit being formed on a wafer. However, it is understood that device 20 may comprise any structure, including ones having one or more ultra thin layers (e.g., approximately 0-30 Å). Device 20 may also comprise thicker films and more complex stacks of films that can be characterized using the techniques described herein, including anisotropic films. In FIG. 1, device 20 represents a step in the formation of a semiconductor device, such as a MOSFET, and comprises a substrate 26, a gate oxide layer 22, and a pseudo substrate 24. Processing system 10 includes a layer forming system 16 for forming gate oxide layer 22, a measuring system 14 for measuring a thickness of the gate oxide layer 22, and a control system 12 for controlling the measuring system 14 and the layer forming system 16.

It is to be appreciated that gate oxide layer 22 can be formed, for example, from oxygen, silicon and nitrogen to form one or more materials including, but not limited to, silicon oxide, silicon nitride and silicon oxynitride layers. It is understood that a gate oxide layer 22 may be a stacked gate oxide sublayer. It is to be further appreciated that such gate oxide layers can be formed by layer forming system 16 by employing techniques including, but not limited to chemical vapor deposition (CVD), rapid thermal oxidation, metalorganic CVD (MOCVD), atomic layer CVD (ALCVD), pulsed laser deposition (PLD), oxide growth and other deposition processes.

Measuring system 14 measures a thickness of gate oxide layer 22 by providing one or more light sources that project light onto respective portions of the layer 22. Light reflected by the gate oxide layer 22 (i.e., an optical response) is collected by one or more light collecting devices and is processed by measuring system 14 to measure at least one parameter relating to the gate oxide layer 22. Measuring system 14 may include any now known or later developed process, e.g., spectroscopic ellipsometry, reflectometry, scatterometry, etc., for implementing such a characterization.

Note that measuring system 14 may also be utilized to characterize other parameters in a layer being analyzed, including chemical properties, e.g., what percentage of the film contains nitrogen, optical constants associated with the materials, etc. Such characterizations may be based on transmittance (i.e., how much light was transmitted) or reflectance (i.e., how much light was reflected).

Figure 2:
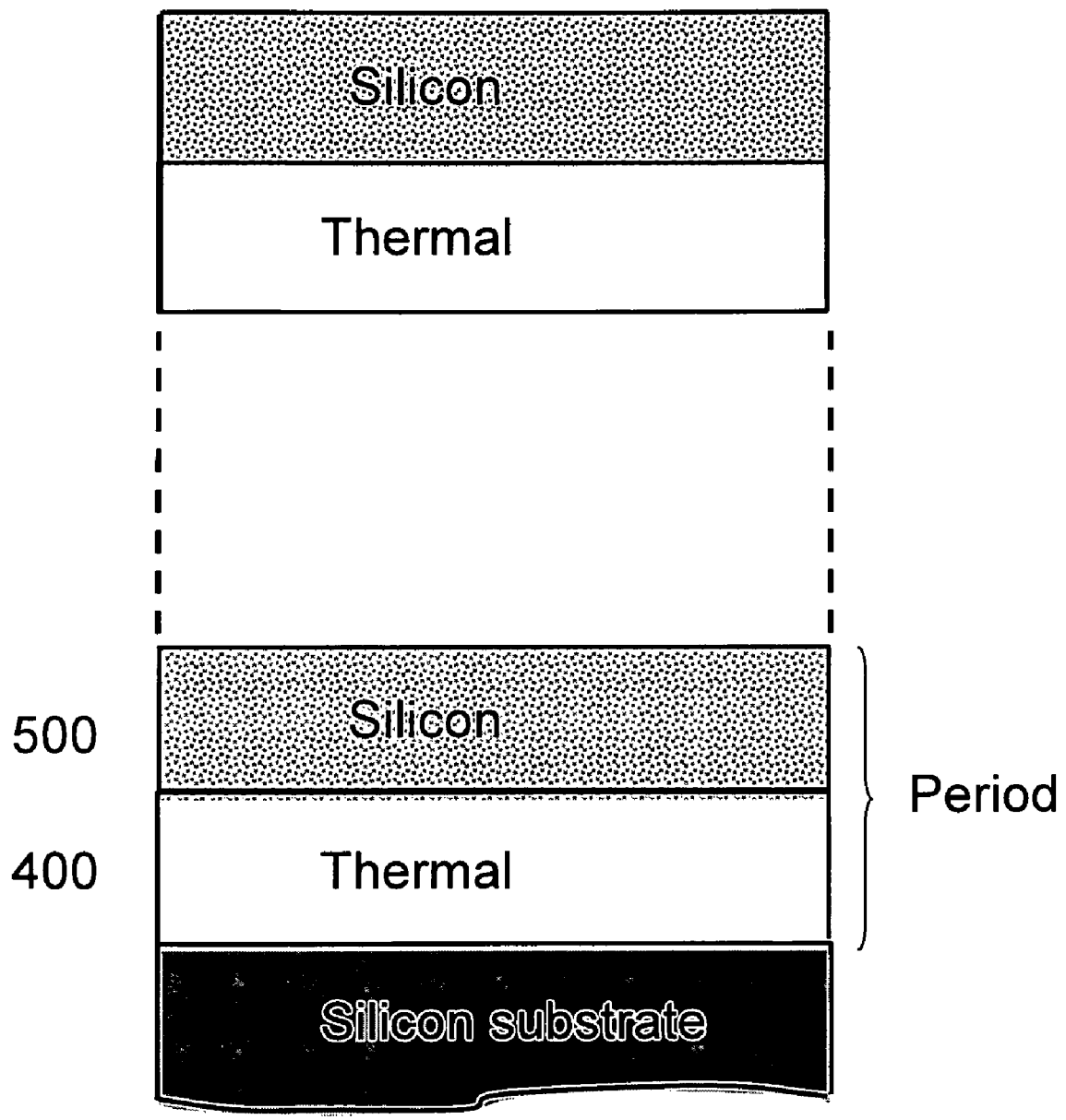
FIG. 2 depicts a Bragg filter implementation in accordance with an embodiment of the present invention.

As noted above, the optical response from ultra thin films may fall below the detection limitations of most existing measuring tools. To address this, the present disclosure provides a pseudo substrate 24 to enhance the optical response to more accurately characterize and measure the thickness of the ultra thin (e.g., gate oxide) layer. FIG. 2 depicts an example of a Bragg reflector that could be used to provide the pseudo substrate 24. A Bragg reflector is an optical mirror obtained by periodically stacking two sublayers with high and low indices of refraction ($n_H$ and $n_L$). The thickness $d_H$ and $d_L$ of the sublayers in each period follow the relations $d_L n_L = d_H n_H = \lambda/4$, where $\lambda$ is the wavelength corresponding to the reflectance maxima.

In the example of FIG. 2, the Bragg reflector includes a plurality of periods of a "silicon-thermal oxide" stack. In this example, silicon and thermal $SiO_2$ provide alternating high and low index of refraction materials, respectively. Note that the pseudo substrate 24 does not necessarily perform any function within the device itself, other than as a means for magnifying the optical response of the ultra thin layer placed on top of it. Also note that the invention is not limited to Bragg reflectors as other types of reflectors could likewise be employed, e.g., a Fabry Perot filter, etc. As such, for the purposes of this disclosure, the term optical mirror refers to any type of reflector or filter.

Figure 3A:
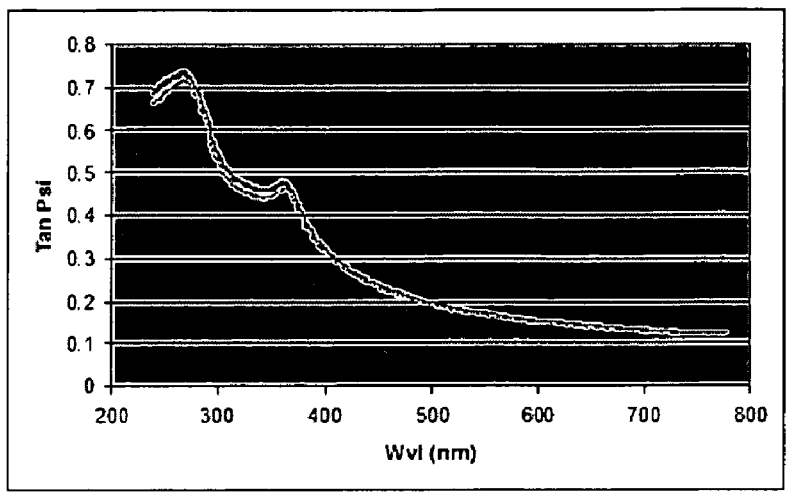
FIG. 3A depicts the Tan(ψ) spectra of gate oxide on silicon.
Figure 3B:
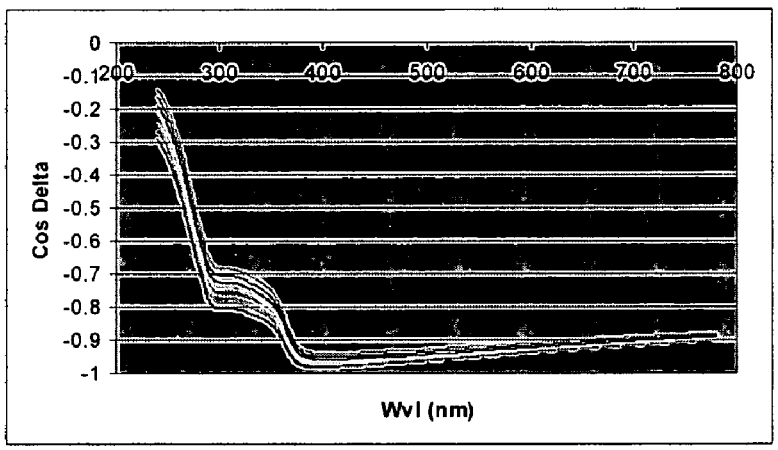
FIG. 3B depicts the Cos(Δ) spectra of gate oxide on silicon.
Figure 3C:
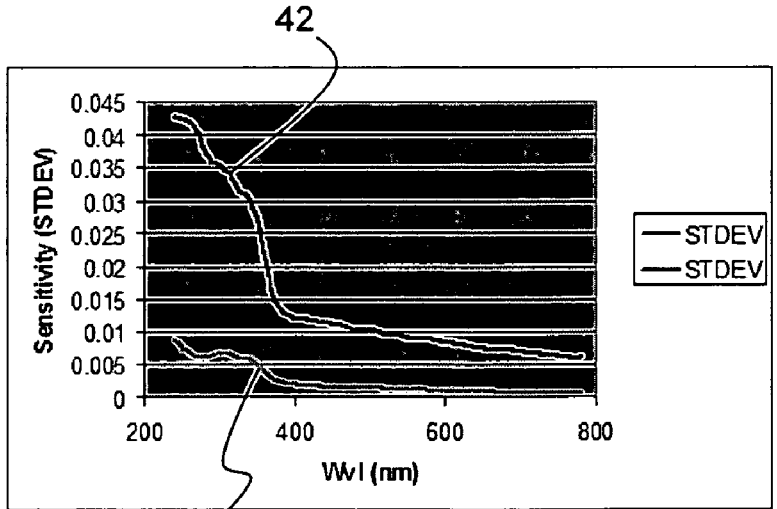
FIG. 3C depicts a sensitivity curve for Tan(ψ) and Cos(Δ) for gate oxide on silicon.

FIGS. 3A and 3B depict the Tan(ψ) and Cos(Δ) spectra of gate oxide on silicon, i.e., without the use of a pseudo substrate 24. Ellipsometric parameters ψ and Δ are known in the art, and are for instance described in the text book, R. M. A. Azzam and N. M. Bashara, Ellipsometry and Polarized Light (North Holland, N.Y., 1987). The gate oxide thickness is in the 0-30 Å range with 5 Å increments. FIG. 3C depicts sensitivity curves 40, 42 for the Tan(ψ) Spectra and Cos(Δ) spectra of FIGS. 3A and 3B, respectively. As can be seen, sensitivity is very low, particularly at wavelengths greater than 400 nanometers. Note that the sensitivity plots are in terms of standard deviation of the spectra shown in FIGS. 3A and 3B. Larger standard deviation means larger spectral variation/response to gate oxide thickness variation and hence more sensitivity to the thickness.

Figure 4A:
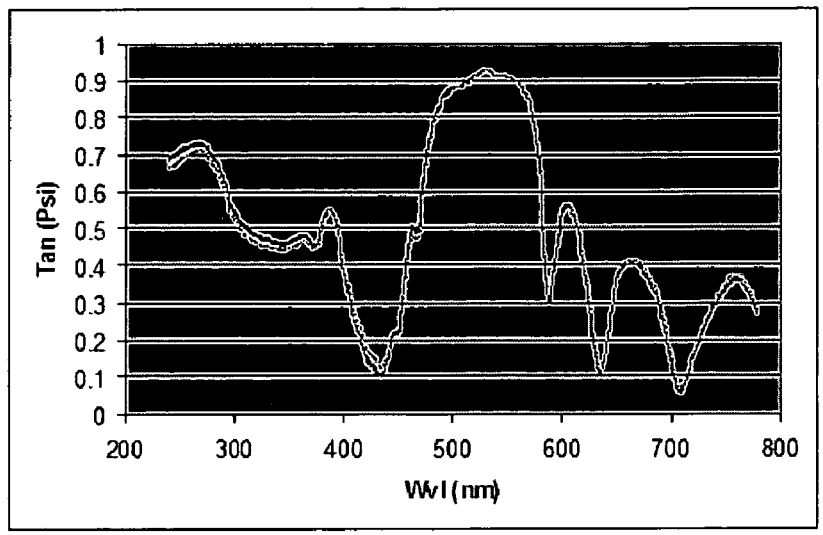
FIG. 4A depicts the Tan(ψ) spectra of gate oxide on a Bragg filter.
Figure 4B:
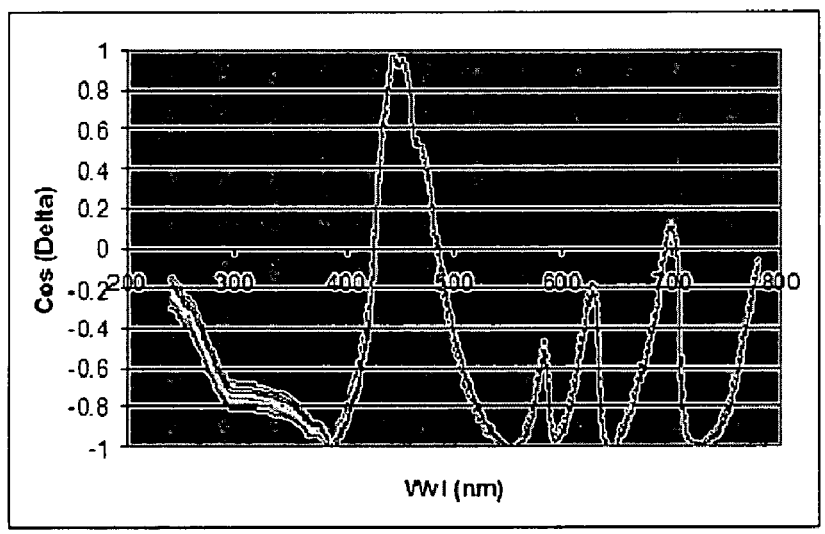
FIG. 4B depicts the Cos(Δ) spectra of gate oxide on a Bragg filter.
Figure 5A:
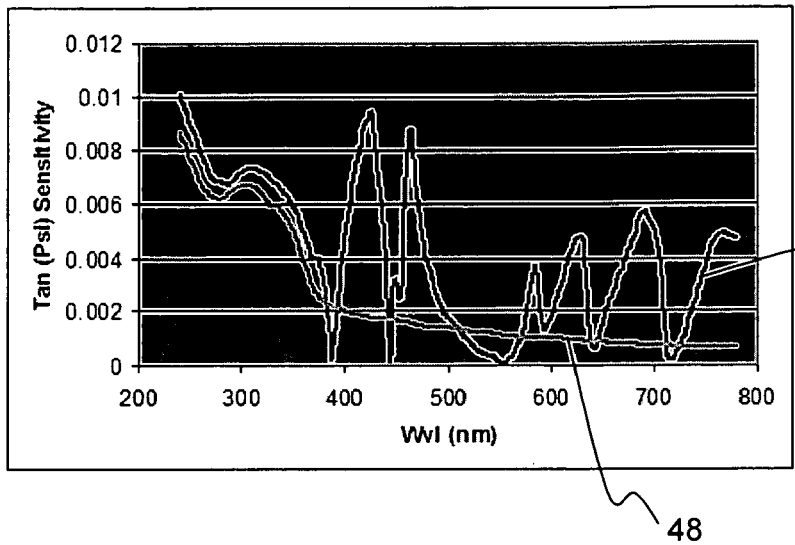
FIG. 5A depicts a sensitivity curve for Tan(ψ) for gate oxide on a Bragg filter.
Figure 5B:
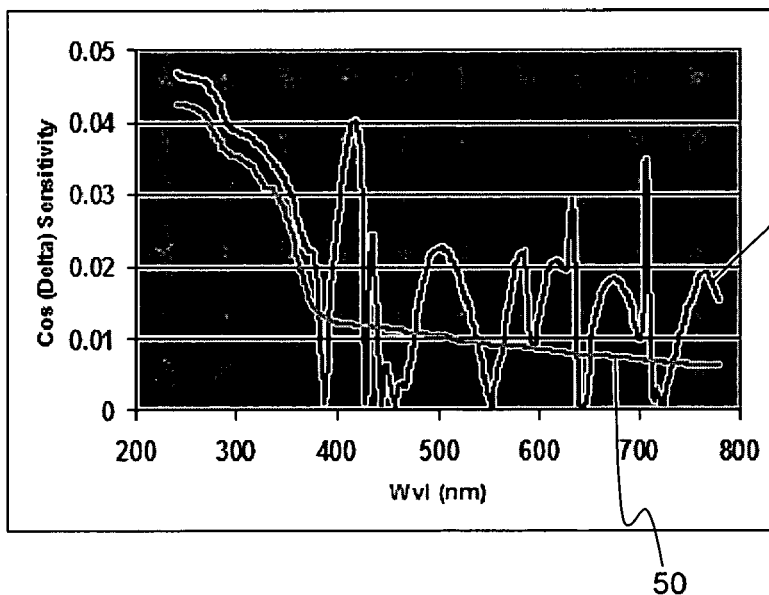
FIG. 5B depicts a sensitivity curve for Cos(Δ) for gate oxide on a Bragg filter.

FIGS. 4A and 4B depict the Tan(ψ) and Cos(Δ) spectra of gate oxide on the Bragg reflector of FIG. 2. The gate oxide thickness is in the 0-30 Å range with 5 Å increments. FIGS. 5A and 5B depict the sensitivity curves 44, 46 for the Tan(ψ) and Cos(Δ) spectra of FIGS. 4A and 4B, respectively. For convenience, sensitivity curves 48, 50 of oxide on silicon are also shown. Note that the gate oxide thickness sensitivity is significantly larger using a pseudo substrate made of a Bragg reflector.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A system for characterizing a film, the system comprising:
    a structure having:
        a substrate; and
        a pseudo substrate positioned below the film and over the substrate,
        wherein the pseudo substrate includes an optical mirror for enhancing an optical response,
        wherein the optical mirror includes a Bragg reflector having at least one period, the at least one period including:
            a layer formed substantially of silicon; and a layer formed substantially of thermal silicon dioxide underlying the layer formed substantially of silicon, wherein a thickness of the layer formed substantially of silicon and a thickness of the layer formed substantially of thermal silicon dioxide have a thickness relationship according to:

$d_L * n_L = d_H * n_H = \lambda/4;$ where $d_H$ is a thickness of the layer formed substantially of silicon, $d_L$ is a thickness of the layer formed substantially of thermal silicon dioxide, where $n_H$ is an index of refraction of the layer formed substantially of silicon, $n_L$ is an index of refraction of the layer formed substantially of thermal silicon dioxide, and $\lambda$ is a wavelength corresponding to a reflectance maxima; and a system for characterizing a parameter of the film by applying a light source to the film and analyzing the optical response.

2. The system of claim 1, wherein the film comprises an ultra thin film having a thickness between 0 and approximately 30 A.

3. The system of claim 2, wherein the structure comprises an integrated circuit and the ultra thin film comprises a gate oxide layer.

4. The system of claim 1, further comprising a layer forming system for forming the film as the film is being characterized.

5. The system of claim 1, wherein the film comprises an anisotropic film.

6. The system of claim 1, wherein the parameter includes a thickness of the film.

7. The system of claim 1, wherein the parameter includes a chemical composition of the film.

8. The system of claim 1, wherein the parameter includes an optical constant associated with the film.

* * * * *